United States Patent [19]

Del Rossi

[11] Patent Number: 5,202,518

[45] Date of Patent: Apr. 13, 1993

[54] LIQUID ACID ALKYLATION CATALYST AND ISOPARAFFIN:OLEFIN ALKYLATION PROCESS

[75] Inventor: Kenneth J. Del Rossi, Woodbury, N.J.

[73] Assignee: Mobil Oil Corporation, Fairfax, Va.

[21] Appl. No.: 761,567

[22] Filed: Sep. 18, 1991

[51] Int. Cl.⁵ .......................... C07C 2/60; C07C 2/62; B01J 27/02

[52] U.S. Cl. .................................. 585/724; 585/723; 585/730; 502/150; 502/170

[58] Field of Search ............... 585/722, 723, 724, 725, 585/730; 502/150, 170

[56] References Cited

U.S. PATENT DOCUMENTS

| | | | |
|---|---|---|---|
| 2,615,908 | 10/1952 | McCaulay et al. | 260/438 |
| 3,531,546 | 9/1970 | Hervert | 260/683.43 |
| 3,778,489 | 12/1973 | Parker et al. | 260/683.43 |
| 3,795,712 | 3/1974 | Chatou et al. | 260/671 |
| 3,856,764 | 12/1974 | Throckmorton et al. | 260/82.1 |
| 4,636,488 | 1/1987 | Imai et al. | 502/172 |
| 4,938,935 | 7/1990 | Audeh et al. | 423/240 |
| 4,938,936 | 7/1990 | Yan | 423/240 |
| 4,985,220 | 1/1991 | Audeh et al. | 423/240 |
| 5,073,674 | 12/1991 | Olah | 585/725 |

OTHER PUBLICATIONS

"Alkylation of Isobutane with C₄ Olefins", 27 *Ind. Eng. Chem. Res.*, 381-397, (1988).
*Handbook of Petroleum Refining Processes*, 23-28 (R. A. Meyers, ed., 1986).

Primary Examiner—Asok Pal
Attorney, Agent, or Firm—Alexander J. McKillop; Dennis P. Santini; Robert B. Furr, Jr.

[57] ABSTRACT

The invention provides an acid catalyst composition for alkylation of an isoparaffin with an olefin comprising from about 10 to about 90 percent of at least one acid selected from the group consisting of hydrofluoric acid and the halogen-substituted sulfonic acids, together with from about 10 to about 90 weight percent of a mono-, di-, or tri-carboxylic acid substituted member selected from the group consisting of alkanes, aromatics, haloalkanes, and haloaromatics having from about 1 to about 30 carbon atoms.

2 Claims, 2 Drawing Sheets

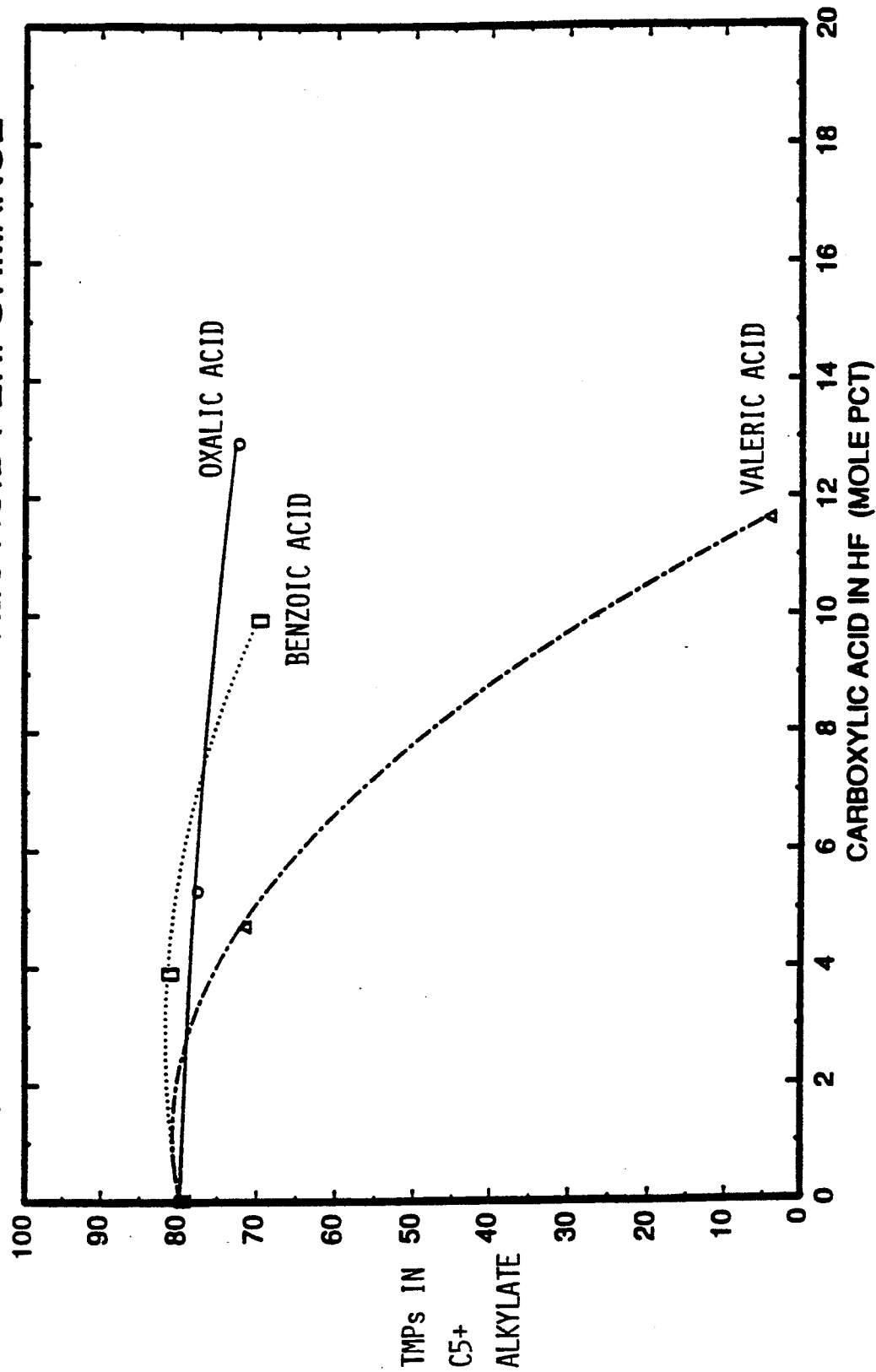

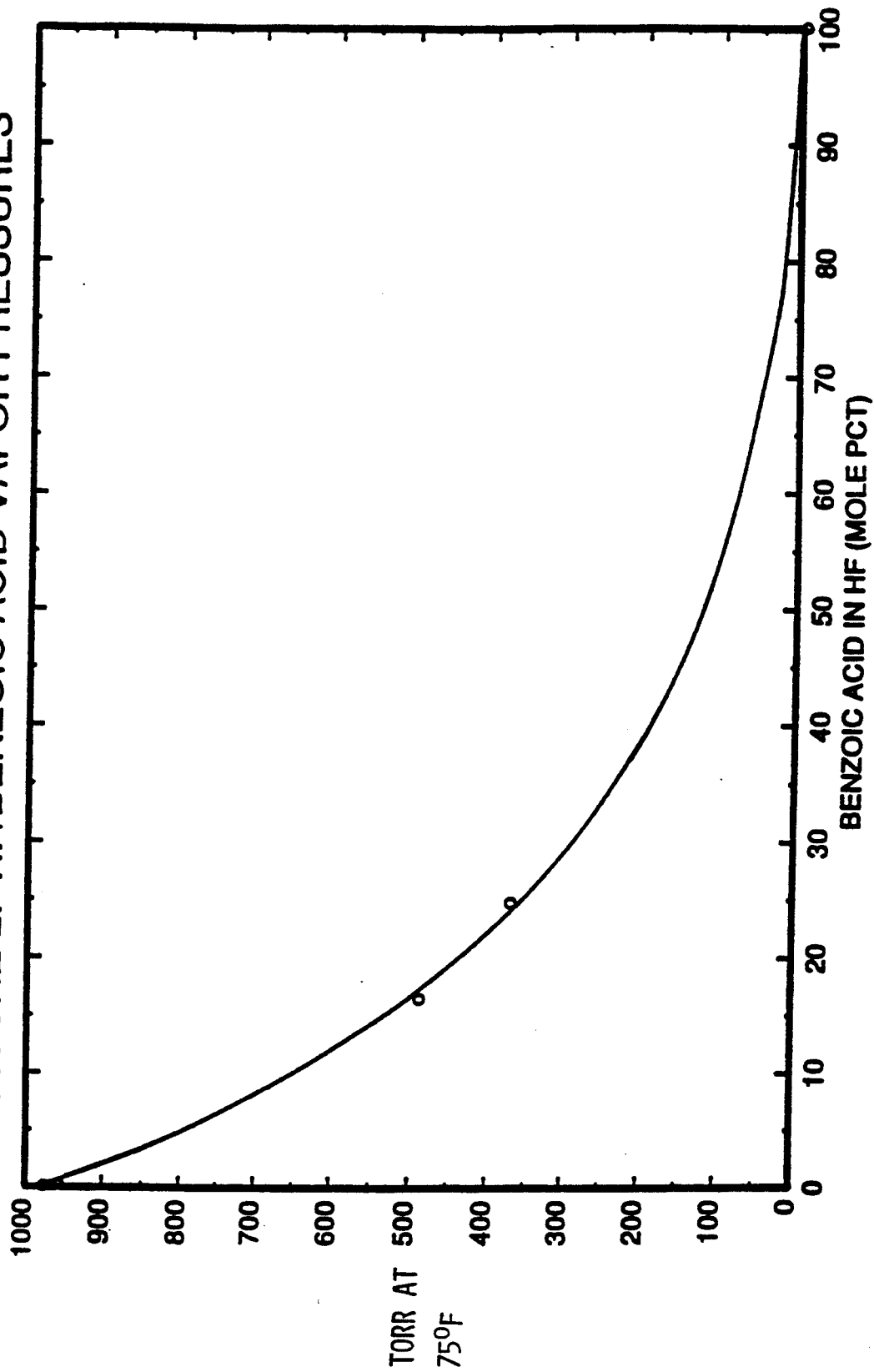

LIQUID ACID ALKYLATION CATALYST AND ISOPARAFFIN:OLEFIN ALKYLATION PROCESS

FIELD OF THE INVENTION

The present invention relates to the art of catalytic alkylation. More specifically, the invention relates to a liquid alkylation catalyst and an isoparaffin:olefin alkylation process. Particularly, the invention provides a liquid alkylation catalyst composition which avoids many of the safety and environmental concerns associated with hydrofluoric acid, particularly with concentrated hydrofluoric acid.

BACKGROUND OF THE INVENTION

Alkylation is a reaction in which an alkyl group is added to an organic molecule. Thus an isoparaffin can be reacted with an olefin to provide an isoparaffin of higher molecular weight. Industrially, the concept depends on the reaction of a $C_2$ to $C_5$ olefin with isobutane in the presence of an acidic catalyst producing a so-called alkylate. This alkylate is a valuable blending component in the manufacture of gasolines due not only to its high octane rating but also to its sensitivity to octane-enhancing additives.

Industrial alkylation processes have historically used concentrated hydrofluoric or sulfuric acid catalysts under relatively low temperature conditions. Acid strength is preferably maintained at 88 to 94 weight percent by the continuous addition of fresh acid and the continuous withdrawal of spent acid. As used herein, the term "concentrated hydrofluoric acid" refers to an essentially anhydrous liquid containing at least about 85 weight percent HF.

Hydrofluoric and sulfuric acid alkylation processes share inherent drawbacks including environmental and safety concerns, acid consumption, and sludge disposal. For a general discussion of sulfuric acid alkylation, see the series of three articles by L. F. Albright et al., "Alkylation of Isobutane with $C_4$ Olefins", 27 *Ind. Eng. Chem. Res.*, 381–397, (1988). For a survey of hydrofluoric acid catalyzed alkylation, see 1 *Handbook of Petroleum Refining Processes* 23–28 (R. A. Meyers, ed., 1986).

Hydrogen fluoride, or hydrofluoric acid (HF) is highly toxic and corrosive. However, it is used as a catalyst in isomerization, condensation, polymerization and hydrolysis reactions. The petroleum industry used anhydrous hydrogen fluoride primarily as a liquid catalyst for alkylation of olefinic hydrocarbons to produce alkylate for increasing the octane number of gasoline. Years of experience in its manufacture and use have shown that HF can be handled safely, provided the hazards are recognized and precautions taken. Though many safety precautions are taken to prevent leaks, massive or catastrophic leaks are feared primarily because the anhydrous acid will fume on escape creating a vapor cloud that can be spread for some distance. Previous workers in this field approached this problem from the standpoint of containing or neutralizing the HF cloud after its release.

U.S. Pat. Nos. 4,938,935 and 4,985,220 to Audeh and Greco, as well as U.S. Pat. No. 4,938,936 to Yan teach various methods for containing and/or neutralizing HF acid clouds following accidental releases.

But it would be particularly desirable to provide an additive which decreases the cloud forming tendency of HF without compromising its activity as an isoparaffin:olefin alkylation catalyst. Solvents and complexing agents for hydroflouric acid complexes have, in the past, been disclosed for various purposes as noted in the following references.

U.S. Pat. No. 2,615,908 to McCaulay teaches thioether-HF-copper complex compounds and a method for preparing the same. Potential uses for the thioether-HF-copper composition compounds are listed from column 6, line 55 through column 8 at line 3. The method is said to be useful for purifying HF-containing vent gases from an industrial HF alkylation plant. See column 7, lines 10–24.

U.S. Pat. No. 3,531,546 to Hervert discloses a $HF-CO_2$ catalyst composition which is said to be useful for alkylation as well as olefin isomerization.

U.S. Pat. No. 3,795,712 to Torck et al. relates to acid catalysts comprising a Lewis acid, a Bronsted acid, and a sulfone of the formula $R-SO_2-R'$, where R and R' are each separately a monovalent radical containing from 1 to 8 carbon atoms or form together a divalent radical having from 3 to 12 carbon atoms.

U.S. Pat. No. 3,856,764 to Throckmorton et al. teaches an olefin polymerization catalyst comprising (1) at least one organoaluminum compound, (2) at least one nickel compound selected from the class consisting of nickel salts of carboxylic acids, organic complex compounds of nickel, or nickel tetracarbonyl and (3) at least one hydrogen fluoride complex prepared by complexing hydrogen fluoride with a member of the class consisting of ketones, ethers, esters, alcohols, nitriles, and water.

U.S. Pat. No. 4,636,488 discloses an anhydrous nonalcoholic alkylation catalyst comprising a mixture of a mineral acid and an ether in proportions of from about 50 to about 99 weight percent of mineral acid and from about 1 to about 50 weight percent of ether. Useful mineral acids include HF; see column 4 at lines 56–60.

U.S. Pat. No. 3,778,489 to Parker et al. teaches that compounds such as alcohols, thiols, water, ethers, thioethers, sulfonic acids, and carboxylic acids can be effectively employed as catalyst promoters in combination with strong Bronsted acids such as HF, fluorosulfonic and trihalomethanesulfonic acids for catalytic isoparaffin:olefin alkylation.

The foregoing references are incorporated by reference as if set forth at length herein, particularly for the details of HF alkylation process operation. In view of the increasing safety and environmental concerns surrounding the cloud-forming tendency of hydrofluoric acid, providing an additive to mitigate HF cloud formation without disturbing the catalytic properties of hydrofluoric acid for isoparaffin:olefin alkylation would clearly be a major advance in the art. Thus one object of the present invention is to provide a catalyst composition which can be substituted for concentrated hydrofluoric acid in a conventional riser-type hydrofluoric acid isoparaffin:olefin alkylation process unit. A further object of the invention is to provide a catalyst composition which provides sufficient acid strength to minimize loss of throughput capacity upon replacing concentrated hydrofluoric acid with the catalyst composition of the invention in an industrial riser-type hydrofluoric acid isoparaffin:olefin alkylation process.

SUMMARY OF THE INVENTION

The carboxylic acids of the present invention have been found to suppress the vapor-forming tendency of strong Bronsted acids such as HF. Surprisingly, however, these carboxylic acids have only minor effects on the isoparaffin:olefin alkylation activity of the strong Bronsted acid. The properties of the carboxylic acids of the invention differ markedly and unexpectedly from other carboxylic acids having similar structures. For example, U.S. Pat. No. 3,778,489 to Parker et al. teaches that some carboxylic acids can promote the isoparaffin:olefin alkylation activity of strong acids such as sulfuric, hydrofluoric, the halosulfuric acids, and the trihalomethanesulfonic acids. But rather than promote isoparaffin:olefin activity, the carboxylic acids of the present invention appear to mildly suppress isoparaffin:olefin activity while markedly decreasing the vapor pressure of the strong Bronsted acid.

The carboxylic acid additives of the invention have further been found to offer desirable process flexibility in that a catalyst composition of the invention containing a carboxylic acid additive may readily be used in an industrial riser-type hydrofluoric acid alkylation process unit as a substitute for the hydrofluoric acid catalyst.

The mechanism underlying the behavior of the class of carboxylic acids useful in the present invention is not well understood. Certain carboxylic acids appear to have little effect on isoparaffin:olefin alkylation activity while various other carboxylic acids suppress or promote the same isoparaffin:olefin alkylation reaction. Thus the behavior of carboxylic acids as a class of additive compounds is difficult to predict. The behavior of the carboxylic acids of the present invention is particularly surprising because years of industrial experience have proven that maintaining acid strength in commercial HF alkylation process units is critical to alkylate product quality, with loss of acid strength precipitating immediate degradation in alkylate product quality.

The invention provides, in a first aspect, an alkylation catalyst composition comprising from about 10 to about 90 weight percent of at least one acid selected from the group consisting of hydrofluoric acid and the halogen-substituted sulfonic acids, together with from about 10 to about 90 weight percent of a mono-, di-, or tri-carboxylic acid substituted alkane, aromatic, haloalkane, or haloaromatic having from about 1 to about 30 carbon atoms, preferably from about 1 to about 10 carbon atoms, more preferably from about 1 to about 6 carbon atoms. The halide-substituted aromatic or alkane may be partially or fully substituted with halide. Examples of useful halogenated sulfonic acids include chlorosulfonic, fluorosulfonic, difluoromethanesulfonic, and the perfluoroalkanesulfonic acids, e.g. trifluoromethanesulfonic acid. Examples of useful carboxylic acid additives include trifluoroacetic, heptafluorobutyric, oxalic, and benzoic acids. As used herein, the term "haloalkane" refers to an alkane having at least one hydrogen replaced by a halogen. Similarly, the term "haloaromatic" as used herein designates an aromatic ring wherein at least one hydrogen is replaced by a halogen.

The invention further provides, in a second aspect, a process for alkylating an isoparaffin with an olefin comprising contacting at least one isoparaffin and at least one olefin with an alkylation catalyst composition comprising from about 10 to about 90 weight percent of at least one acid selected from the group consisting of hydrofluoric acid and the halogen-substituted sulfonic acids, together with from about 10 to about 90 weight percent of a mono-, di-, or tri-carboxylic acid substituted alkane, aromatic, haloalkane, or haloaromatic having from about 1 to about 30 carbon atoms, preferably from about 1 to about 10 carbon atoms, more preferably from about 1 to about 6 carbon atoms.

DESCRIPTION OF THE DRAWINGS

FIG. 1 shows the isoparaffin:olefin alkylation performance of HF together with oxalic, benzoic, and valeric acids. Trimethylpentane content in the $C_5$+alkylate product (the y-axis) declines as the carboxylic acid content of the HF/carboxylic acid catalyst (the x-axis) increases. Oxalic and benzoic acids (shown by the circular and rectangular data points, respectively) dilute the HF acid without markedly diminishing isoparaffin:olefin alkylation performance, but the valeric acid (a straight chain alkyl carboxylic acid, shown by the triangular data points) suppresses HF alkylation catalyst performance.

FIG. 2 illustrates the effectiveness of benzoic acid as a vapor pressure suppressant for HF, showing vapor pressure (in units of Torr at 75° F., shown on the y-axis) as a function of benzoic acid concentration in HF (mole percent, shown on the x-axis).

DETAILED DESCRIPTION

Feedstocks

Feedstocks useful in the present alkylation process include at least one isoparaffin and at least one olefin. The isoparaffin reactant used in the present alkylation process has from about 4 to about 8 carbon atoms. Representative examples of such isoparaffins include isobutane, isopentane, 3-methylhexane, 2-methylhexane, 2,3-dimethylbutane and 2,4-dimethylhexane.

The olefin component of the feedstock includes at least one olefin having from 2 to 12 carbon atoms. Representative examples of such olefins include butene-2, isobutylene, butene-1, propylene, ethylene, hexene, octene, and heptene, merely to name a few. The preferred olefins include the $C_4$ olefins, for example, butene-1, butene-2, isobutylene, or a mixture of one or more of these $C_4$ olefins, with butene-2 being the most preferred. Suitable feedstocks for the process of the present invention are described in U.S. Pat. No. 3,862,258 to Huang et al. at column 3, lines 44–56, the disclosure of which is incorporated by reference as if set forth at length herein.

The molar ratio of isoparaffin to olefin is generally from about 1:1 to about 100:1, preferably from about 1:1 to about 50:1, and more preferably from about 5:1 to about 20:1.

Catalyst Composition

The catalyst composition of the present invention comprises from about 10 to about 90 weight percent of at least one acid selected from the group consisting of hydrofluoric acid and the halogen-substituted sulfonic acids, and from about 10 to about 90 weight percent of a mono-, di-, or tri-carboxylic acid substituted alkane, aromatic, haloalkane, or haloaromatic having from about 1 to about 30 carbon atoms, preferably from about 1 to about 10 carbon atoms, more preferably from about 1 to about 6 carbon atoms. The halide-substituted aromatic or alkane may be partially or fully substituted with halide. Halogenated carboxylic acids are preferred, and trifluoroacetic acid and heptafluorobutyric acids are more preferred.

The alkylation catalyst composition of the invention preferably comprises from about 10 to about 90 weight percent additive, more preferably from about 20 to about 80 weight percent additive, with the substantial balance of the catalyst composition comprising the strong Bronsted acid. The catalyst composition of the invention is preferably free of intentionally added water, and still more preferably, is anhydrous.

Process Conditions

The catalyst composition of the present invention may be readily substituted for the concentrated hydrofluoric acid catalyst in an existing hydrofluoric acid alkylation process without substantial equipment modifications. Accordingly, the conversion conditions for the process of the present invention resemble those of typical commercial hydrofluoric acid alkylation processes. The present alkylation process is suitably conducted at temperatures of from about 10° to about 100° C., preferably from about 20° to about 80° C., and more preferably from about 25° C. to about 40° C. to avoid undesirable side reactions. Pressure is maintained to ensure a liquid phase in the alkylation reaction zone, typically falling within the range of from about 20 to about 1,200 psig, and preferably are within the range of from about 50 to about 500 psig. Olefin feed rates can vary from 0.01 to 10 weight hourly space velocity (WHSV), and are preferably from about 0.05 to about 5 WHSV. Contact times for isoparaffin:olefin feed with the catalyst composition of the present invention can range from about 0.1 second to about 100 minutes, and more preferably are from about 10 seconds to about 20 minutes.

The alkylation reaction may be conducted in any suitable reactor vessel, for example, a stirred tank or a riser-type reactor. While the scope of the present invention is not limited by reactor configuration, the catalyst composition of the invention may readily be used in existing conventional riser-reactor hydrofluoric acid isoparaffin:olefin alkylation process units as a substitute for concentrated hydrofluoric acid.

The additive component of the catalyst composition may be injected directly into the alkylation process unit. Alternatively, the additive component may be mixed with either the hydrocarbon charge or the fresh and/or circulating acid component of the catalyst composition. Downstream from the alkylation reaction zone, the additive component is preferably separated from the alkylate product stream, mixed with fresh acid and/or circulating catalyst, and recycled to the alkylation reaction zone. The particular separation technique selected, however, depends at least in part upon the type of carboxylic acid. For instance, low boiling carboxylic acids, such as trifluoroacetic acid, may be recovered by distillation. High boiling carboxylic acids may need to be recovered by other techniques such as liquid-liquid extraction or ion exchange.

In a typical commercial embodiment, the effluent stream from the alkylation reaction zone is separated, e.g., decanted, into an alkylate-rich hydrocarbon stream and an acid recycle stream. The alkylate-rich hydrocarbon stream is typically fractionated further to provide an isoparaffin recycle stream to the alkylation reaction zone. In the present invention, the preferred method for recycling the carboxylic acid additive to the alkylation reaction zone varies with the particular carboxylic acid employed. Decanting the alkylation reaction zone effluent to separate alkylate-rich hydrocarbon from the HF/carboxylic acid mixture has been found to yield relatively pure hydrocarbon and HF/carboxylic acid streams. However, some carboxylic acids of the invention having, for example, valeric acid, are partitioned between the alkylate-rich hydrocarbon stream and the HF/carboxylic acid streams upon decantation, and the resulting hydrocarbon stream must be further purified to recover the carboxylic acid. The extent of partitioning increases with increasing carbon number of the carboxylic acid, and is clearly evident with valeric acid and the heavier alkyl carboxylic acids (having 5 or more carbon atoms). Suitable purification techniques include distillation of the alkylate from the carboxylic acid as well as solvent extraction of the carboxylic acid from the alkylate with a suitable solvent, for example, water or alcohol.

EXAMPLES

The following Examples 1-11 demonstrate the effectiveness of the catalyst composition of the invention for catalyzing isoparaffin:olefin alkylation. Example 1 demonstrates the well-known effectiveness of anhydrous HF as an isoparaffin:olefin alkylation catalyst and is presented for comparison to evaluate the effectiveness of various carboxylic acid additives (Examples 2-11).

EXAMPLE 1—COMPARATIVE

Anhydrous HF (40 grams, obtained from Matheson Chemical Company of Bridgeport, N.J.) was condensed into a clean, dry autoclave (1,000 cc). Isobutane (100 grams) was added, and the autoclave was stirred at 1,500 rpm. The autoclave was brought to room temperature (22° C., 71° F.) and pressurized to 100 psig. A pre-mixed 10:1 weight:weight mixture of isobutane:2-butene feed (obtained from Matheson Chemical Company) was added at a rate of 250 cc/hour for 2 hours under autogeneous pressure for a total isobutane:2-butene charge of 500 cc. A 8°-12° F. (4°-7° C.) temperature rise was observed during feed addition resulting in an average reaction temperature of 79°-83° F. (26°-28° C.). The autoclave was sampled (300 cc) immediately after feed addition was complete. The sample was flashed at room temperature and quenched with a chilled water trap. Samples of the liquid and gas products were analyzed by capillary GC (60m DB-1 column). The results of Example 1 are shown in the table below.

EXAMPLE 2—HF/VALERIC ACID

Ten (10) grams of chilled valeric acid was added to a clean, dry autoclave (1,000 cc). The autoclave was sealed, cooled with liquid nitrogen and placed under vacuum. Anhydrous HF (40 grams, obtained from Matheson Chemical Company of Bridgeport, N.J.) was then condensed into the autoclave. Isobutane (100 grams) was added, and the autoclave was stirred at 1,500 rpm. The autoclave was brought to room temperature (22° C., 71° F.) and pressurized to 100 psig. A pre-mixed 10:1 weight:weight mixture of isobutane:2-butene feed (obtained from Matheson Chemical Company) was added at a rate of 250 cc/hour for 2 hours under autogeneous pressure for a total isobutane:2-butene charge of 500 cc. A 8°-12° F. (4°-7° C.) temperature rise was observed during feed addition resulting in an average reaction temperature of 79°-83° F. (26°-28° F.). The autoclave was sampled (300 cc) immediately after feed addition was complete. The sample was flashed at room temperature and quenched with a chilled water trap. Samples of the liquid and gas products were analyzed by capillary GC (60m DB-1 column). Results of Example 2 are reported in the table below.

EXAMPLES 3-11

The above procedure was repeated with a higher concentration of valeric acid (Example 3), HF/benzoic acid (Examples 4 and 5), HF/oxalic acid (Example 6 and 7), and HF/trifluoroacetic acid (Examples 8-11). The table below summarizes the results from these experiments, showing that while the claimed carboxylic acids (e.g., oxalic, benzoic, and particularly trifluoroacetic) provided effective isoparaffin:olefin alkylation catalysis in the presence of HF, the straight chain unsubstituted carboxylic acid (valeric) proved detrimental to HF acid alkylation performance.

FIG. 2 illustrates the effectiveness of benzoic acid as a vapor pressure suppressant for HF, showing vapor pressure (in units of Torr at 75° F., shown on the y-axis) as a function of benzoic acid concentration in HF (mole percent, shown on the x-axis).

While it is clear that the claimed catalyst compositions exhibit commercially useful isoparaffin:olefin alkylation activity while effectively suppressing the vapor pressure of HF, the reasons why this particular class of carboxylic acids differ so markedly in behavior from the straight chain unsubstituted alkyl carboxylic acids remains unclear. Accordingly, the scope of the present invention is not to be limited by any recitation of theory, but only by the scope of the appended claims.

TABLE

| Example | 1 | 2 | 3 | 4 | 5 | 6 |
|---|---|---|---|---|---|---|
| Carboxylic Acid Additive | None | Valeric | Valeric | Benzoic | Benzoic | Oxalic |
| HF/Carboxylic Acid Ratio (wt/wt) | — | 80/20 | 60/40 | 80/20 | 60/40 | 80/20 |
| Trimethylpentane Yield (wt %) | 81.4 | 72.1 | 5 | 81.4 | 70 | 77.9 |

| Example | 7 | 8 | 9 | 10 | 11 |
|---|---|---|---|---|---|
| Carboxylic Acid Additive | Oxalic | TFA | TFA | TFA | TFA |
| HF/Carboxylic Acid Ratio (wt/wt) | 60/40 | 80/20 | 60/40 | 40/60 | 20/80 |
| Trimethylpentane Yield (wt %) | 72.8 | 84 | 86.9 | 82.9 | 0 |

Changes and modifications in the specifically described embodiments can be carried out without departing from the scope of the invention which is intended to be limited only by the scope of the appended claims.

What is claimed is:

1. An acid catalyst composition for alkylation of an isoparaffin with an olefin comprising from about 40 to about 90 percent hydrofluoric acid together with from about 10 to about 60 weight percent of a carboxylic acid having the formula R—COOH wherein R is $C_6H_5$ or $CF_3$.

2. A process for alkylating an isoparaffin with an olefin comprising effecting reaction of isoparaffin and olefin with an alkylation catalyst composition comprising from about 40 to about 90 percent hydrofluoric acid together with from about 10 to about 60 weight percent of a carboxylic acid having the formula R—COOH wherein R is $C_6H_5$ or $CF_3$.

* * * * *